(12) United States Patent
Bernardini et al.

(10) Patent No.: US 11,864,538 B2
(45) Date of Patent: Jan. 9, 2024

(54) MICROBIOLOGICAL SCREENING DEVICE, IN PARTICULAR FOR THE COLLECTION AND CONCENTRATION OF ORGANIC AND INORGANIC MATERIAL PRESENT IN A LIQUID, AND APPARATUS FOR BREEDING LABORATORY AQUATIC ANIMALS PROVIDED WITH SAID DEVICE

(71) Applicant: TECNIPLAST S.P.A., Buguggiate (IT)

(72) Inventors: Pietro Bernardini, Casciago (IT); Marco Brocca, Tradate (IT); Carmelo Di Martino, Jerago con Orago (IT); Gianpaolo Milite, Udine (IT)

(73) Assignee: TECNIPLAST S.P.A., Buguggiate (IT)

( * ) Notice: Subject to any disclaimer, the term of this patent is extended or adjusted under 35 U.S.C. 154(b) by 42 days.

(21) Appl. No.: 17/213,976

(22) Filed: Mar. 26, 2021

(65) Prior Publication Data

US 2021/0307302 A1    Oct. 7, 2021

(30) Foreign Application Priority Data

Apr. 3, 2020   (IT) .................. 102020000007180

(51) Int. Cl.
| | | |
|---|---|---|
| *A01K 63/04* | (2006.01) | |
| *G01N 1/40* | (2006.01) | |
| *G01N 33/18* | (2006.01) | |

(52) U.S. Cl.
CPC ........... *A01K 63/04* (2013.01); *G01N 1/4077* (2013.01); *G01N 33/1826* (2013.01); *G01N 2001/4088* (2013.01)

(58) Field of Classification Search
CPC .......... A01K 63/04; A01K 61/90; G01N 1/34; G01N 1/40; G01N 1/4005; C12M 1/12;
(Continued)

(56) References Cited

U.S. PATENT DOCUMENTS

| | | | | |
|---|---|---|---|---|
| 3,832,854 A | * | 9/1974 | Metts ....................... | G05D 9/02 137/577 |
| 4,356,791 A | * | 11/1982 | Ward ..................... | B01D 29/05 119/14.33 |

(Continued)

FOREIGN PATENT DOCUMENTS

WO    2014/182027 A1    11/2014

OTHER PUBLICATIONS

Search Report dated Jan. 19, 2021 for corresponding Italian patent application No. 102020000007180.
(Continued)

*Primary Examiner* — Brady W Frazier
*Assistant Examiner* — Zoe Tam Tran
(74) *Attorney, Agent, or Firm* — AMSTER, ROTHSTEIN & EBENSTEIN (57) ABSTRACT

A microbiological screening device, in particular for the collection and concentration of organic and inorganic matter present in a liquid, said device comprising a plurality of hollow tubular sections arranged one following the other, and mutually connected, to define a main hollow tubular body adapted to allow the flowing of a fluid between a first end thereof and a second end thereof, opposite to said one first end thereof, wherein every hollow tubular section comprises a filtering mesh or net arranged substantially transversely to the longitudinal extension direction thereof and including a plurality of through holes.

14 Claims, 7 Drawing Sheets

(58) Field of Classification Search
CPC .......... C12M 1/126; C12M 1/14; C12M 1/16; B01L 2200/0631; B01D 2201/184; B01D 2201/188; B01D 29/0047; B01D 29/0052; B01D 29/0054; B01D 29/0059; B01D 29/56; B01D 29/58
USPC ........................................................ 119/200
See application file for complete search history.

(56) References Cited

U.S. PATENT DOCUMENTS

| | | | | |
|---|---|---|---|---|
| 4,731,177 | A * | 3/1988 | Hemman | B01D 29/03 210/94 |
| 4,816,148 | A * | 3/1989 | Hemman | B01D 29/03 210/256 |
| 11,389,752 | B2 * | 7/2022 | Kawaguchi | B01D 35/34 |
| 2003/0070975 | A1 | 4/2003 | Hogan et al. | |
| 2008/0141587 | A1 * | 6/2008 | Guthrie | A01G 9/028 47/86 |
| 2008/0213877 | A1 * | 9/2008 | Hicks | B01D 29/58 435/309.1 |
| 2012/0055862 | A1 * | 3/2012 | Parekh | C02F 1/42 210/244 |
| 2017/0120237 | A1 * | 5/2017 | McCully | C12M 47/06 |
| 2017/0128863 | A1 * | 5/2017 | Hull | B01D 29/05 |
| 2018/0263192 | A1 * | 9/2018 | Irwin | A01G 25/167 |
| 2019/0141964 | A1 | 5/2019 | Perslow et al. | |
| 2020/0187465 | A1 * | 6/2020 | Oskarsson | A22C 29/043 |
| 2021/0060457 | A1 * | 3/2021 | Ikeda | C12M 1/12 |
| 2022/0104443 | A1 * | 4/2022 | Chang | A47B 47/045 |

OTHER PUBLICATIONS

Anonymous: "SE GP2-9 Set 9-Piece Set of Patented Stackable 13-¼" Sifting Pans" 2016, XP055765256; Retreived from the Internet: URL:http://findgoldtreasure.com/gold-treasure/product/se-gp2-9-set-9-piece-set-of-patented-stackable-13-14-sifting-pans/ [retrieved on Jan. 14, 2021].

Anonymous:"Plankton Screens with medium diameter from 6 to 2000 m", Oct. 2018 (Oct. 2018), XP055765294, Retrieved from the Internet: URL:http://www.aquacare-shop.de/epages/79654597.sf/en_GB/?PbjectPath=/Shops/79654597/Products/Sieb100 [retrieved on Jan. 14, 2021].

EP Office Action dated Nov. 15, 2023 for EP Application No. 21166271.3 filed Mar. 31, 2021.

Steiner Bigna et al: "Instructions for a do-it-yourself sieving station type RAKO for the field", May 30, 2017 (May 30, 2017), XP093100380, Retrieved from the Internet: URL:htps://ipna.duw.unibas.ch/fileadmin/user_upload/ipna_duw/PDF_s/AB_PDF/Sieving_Station.pdf [retrieved on Nov. 10, 2023].

* cited by examiner

MICROBIOLOGICAL SCREENING DEVICE, IN PARTICULAR FOR THE COLLECTION AND CONCENTRATION OF ORGANIC AND INORGANIC MATERIAL PRESENT IN A LIQUID, AND APPARATUS FOR BREEDING LABORATORY AQUATIC ANIMALS PROVIDED WITH SAID DEVICE

FIELD OF THE INVENTION

The present invention relates to the technical field of breeding (housing) laboratory animals, in particular laboratory aquatic animal species. In particular, the present invention relates to the microbiological screening of the breeding water of said laboratory aquatic animal species. In detail, the present invention relates to a device for the microbiological screening of water in systems and/or equipment for housing aquatic animal species. The present invention also relates to an apparatus for breeding laboratory aquatic animal species provided with said device.

BACKGROUND ART

According to the most widespread and commonly adopted solutions, laboratory aquatic animal species are bred in apparatuses including a plurality of trays, arranged for example on the shelves of a shelving, and each intended to house a predefined number of small fish, where the breeding water is circulated between the trays by a special circuit including pipes, pumps, filters and devices adapted to the purpose, substantially known per se and therefore not described in detail for synthesis purposes.

The need to avoid and/or prevent and/or remove, in apparatuses of the aforementioned type, any contamination of the maintenance water which could seriously compromise the health of the animals is therefore evident, where the preventive and/or diagnostic measures most commonly adopted involve the use of animals known as "sentinel" or "colony" animals.

Programs using sentinel fish are developed and designed to maximize the transmission of pathogens to a small group of animals exposed to wastewater from recirculating housing plants.

The sentinel fish can be identified from the colony itself, they can be particularly elderly individuals or they can be specifically selected to be used for health monitoring analyses. To date, specific genetic lines for broad-spectrum health monitoring are difficult to identify.

These specimens must be exposed to recirculating wastewater for a minimum period of three months and be analyzed at least 2/4 times a year.

It is possible to use a combination of analysis methods on fish used as sentinels, which include, by way of non-limiting example, microbiological, PCR and histopathological techniques.

However, the use of sentinel animals (hereinafter "the sentinels") has several drawbacks which the patentee of the present application intends to overcome or at least minimize.

Firstly, a first drawback encountered in the use of sentinel animals is related to the non-negligible risk of transmission of the various pathogens from infected to non-infected subjects, and therefore to the risk of promoting the spread of microbiological positivity.

Furthermore, the need to sacrifice animals dedicated to the purpose (sentinels) or colony animals has a significant impact at the ethical level and therefore in the operational choices for health screening.

Furthermore, the use of animals for microbiological screening has an often non-negligible economic impact due to the maintenance thereof for more or less prolonged periods.

Finally, it cannot be underestimated that a limited number of subjects from the colony are sampled for microbiological screening purposes, where this number is not necessarily representative of the prevalence in the colony of all possible and known infections in aquatic species. The number of subjects to be sampled as a function of statistical confidence levels to ensure that at least one subject sampled is positive for the microorganism sought is dependent on the prevalence of the infection in the colony, a prevalence which is sometimes very low and, in many cases, not even known.

Alternative solutions to the use of sentinel animals according to the background art include the extemporaneous sampling of biological material from different points of the housing system. However, even these extemporaneous sampling solutions do not allow a reliable and low cost microbiological screening of the housing water, nor in an easily implemented manner.

OBJECTS OF THE PRESENT INVENTION

Therefore, the primary object of the present invention is to provide a solution which allows to overcome or at least reduce the disadvantages and/or drawbacks encountered in the microbiological screening and/or monitoring techniques according to the background art.

In particular, the object of the present invention is to provide a microbiological screening and/or monitoring device which ensures reliable monitoring of the housing water of aquatic animal species, in particular laboratory animals, which is achievable and implementable at low costs and according to simple, if not immediate, methods which do not involve the use of sentinel animals, and which last but not least prevents the transmission of pathogens.

DESCRIPTION OF THE PRESENT INVENTION

The present invention arises from the general consideration according to which the above objects can be achieved and the disadvantages found in the solutions according to the background art can be effectively reduced by promoting the forming of a film or substrate of organic material and/or inorganic material coming from the housing water, where said film is easily withdrawable and adapted to be subjected to laboratory analyses.

The present invention has therefore been conceived with the aim of favoring the accumulation in the form of film or substrate of organic and/or inorganic material possibly present in the housing water, and to allow easier handling and without risk of contamination of said film or substrate.

Therefore, based on both of the preset objects summarized above and the above considerations and/or the problems or disadvantages encountered in the solutions according to the background art, the present invention relates to a device and an apparatus, embodiments of the present invention being defined by the claims.

According to an embodiment described, the microbiological screening device according to the present invention is adapted to be applied to an apparatus for housing (breeding, maintenance or housing) aquatic animal species, in particular laboratory animals, so as to intercept at least in part the housing water circulating in the apparatus, as well as in order to capture organic and/or inorganic material, if present in the housing water, in particular by favoring the accumulation of said organic and/or inorganic material in the form of film or substrate which is easily to handle and subject to laboratory exams and/or tests.

According to a described embodiment, the microbiological screening device, in particular for the collection and concentration of organic and inorganic material present in a liquid, comprises a plurality of hollow tubular sections arranged one following the other and mutually connected to define a main hollow tubular body adapted to allow the flowing of a fluid between a first end thereof and a second end thereof opposite to said first end thereof, where every hollow tubular section comprises a filtering mesh arranged substantially transversely to the longitudinal extension direction thereof and comprising a plurality of through holes; where the size of said through holes of each of said filtering meshes is larger than that of the through holes of the subsequent filtering mesh in the direction from said first end to said second end.

According to a described embodiment, each of said filtering meshes is made of polyester and is adapted to promote the forming of a biofilm usable for microbiological investigations.

According to a described embodiment, the outside wall of each of said hollow tubular sections, i.e., the outside wall supporting the filtering mesh, is made entirely of polystyrene.

According to a described embodiment, said hollow tubular sections are mutually connected by form and dimension interference and mutually disconnectable.

According to a described embodiment, each of said hollow tubular sections comprises a first end portion and a second end portion opposite to said first end portion, where said first end portion of each of said sections is adapted to accommodate by form and dimension interference said second end portion of the adjacent hollow tubular section in the direction from said first end to said second end of said main hollow body.

According to a described embodiment, each of said hollow tubular sections comprises an overflow device adapted to allow the flowing of said liquid from the inside of said hollow tubular section to the outside of said hollow tubular section.

According to a described embodiment, each of said overflow devices comprises a through notch made on the outside wall of the respective hollow tubular section, where said through notch extends from the free edge of said first end portion.

According to a described embodiment, said device comprises a hollow container, where said main hollow body formed by said hollow tubular sections is accommodated inside said hollow container.

According to a described embodiment, said device comprises a first plug and a second plug removably applied to a first end portion of said hollow container and to the second end portion of said hollow container, respectively, opposite to said first end portion thereof, where said first plug and second plug comprise a first through-hole and a second through-hole adapted to allow the intake of said liquid into said hollow container and the outflow of said liquid from said hollow container, respectively.

According to a described embodiment, said hollow container comprises means adapted to allow the application thereof to a main pipe and to put in communication the inside of said main pipe with the inside of said main hollow body so as to allow the flowing of said liquid from said main pipe into said main hollow body.

According to a described embodiment, said device comprises three hollow tubular sections, the dimension (diameter) of the through-holes of the filtering mesh of a first hollow tubular section is between 1750 and 2150 μm, where the dimension (diameter) of the through-holes of the filtering mesh of the second hollow tubular section adjacent to said first hollow tubular section is between 55 and 155 μm, and where the dimension (diameter) of the through-holes of the filtering mesh of the third hollow tubular section adjacent to said second hollow tubular section is between 4 and 10 μm.

According to a described embodiment, said device comprises four hollow tubular sections, where the dimension (diameter) of the through-holes of the filtering mesh of a first hollow tubular section is between 1750 and 2150 μm, where the dimension (diameter) of the through-holes of the filtering mesh of the second hollow tubular section adjacent to said first hollow tubular section is between 55 and 155 μm, and where the dimension of the through-holes of the filtering mesh of the third hollow tubular section adjacent to said second hollow tubular section is between 4 and 10 μm.

An apparatus for breeding laboratory aquatic animal species is also described, said apparatus comprising a plurality of trays each adapted to contain a predefined amount of a liquid and to house a subpopulation of said animal species, where said trays are mutually connected by means of a circuit adapted to allow the circulation of said liquid between said trays, where said apparatus comprises at least one device according to one of the described embodiments applied to said circuit so as to intercept at least part of the liquid in transit or circulating within said circuit.

According to a described embodiment, said device is applied to said circuit in a position which allows the flowing by gravity of said liquid within said main hollow body.

According to a described embodiment, said trays are arranged on a shelving including superimposed shelves.

BRIEF DESCRIPTION OF THE FIGURES

A description will be given below of the embodiments of the present invention depicted in the drawings, in which.

It must be noted that the present invention is not limited to the embodiments described below and depicted in the accompanying drawings; on the contrary, all the variants and/or changes to the embodiments described below and depicted in the accompanying drawings will appear obvious and immediate to a person skilled in the art.

DETAILED DESCRIPTION OF THE PRESENT INVENTION

The present invention finds particularly advantageous application in the microbiological screening of the maintenance water (breeding, housing) of aquatic animal species, in particular for laboratory animals, this therefore being the reason why, in the following, the present invention will be described with particular reference to the applications thereof in the field of breeding (maintenance, housing) aquatic animal species, in particular laboratory animals.

However, it is worth specifying that the possible applications of the present invention are not limited to those described below. On the contrary, the present invention finds convenient application in all cases in which it is necessary to optimize the screening and/or microbiological monitoring of a liquid, for example water, capable of containing organic and/or inorganic material.

Figure 1A:
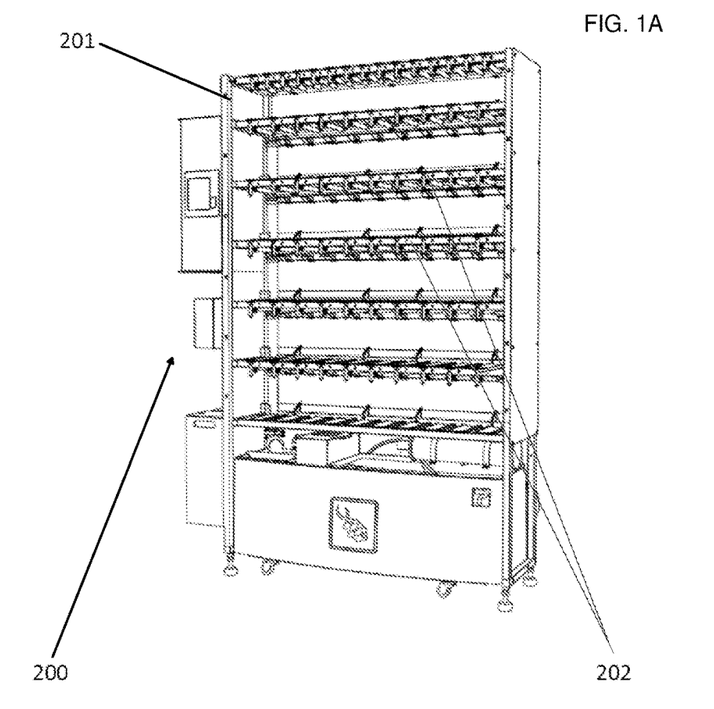
FIGS. 1A and 1B each show a perspective view of an apparatus for the maintenance (breeding, housing) of aquatic animal species.
Figure 1B:
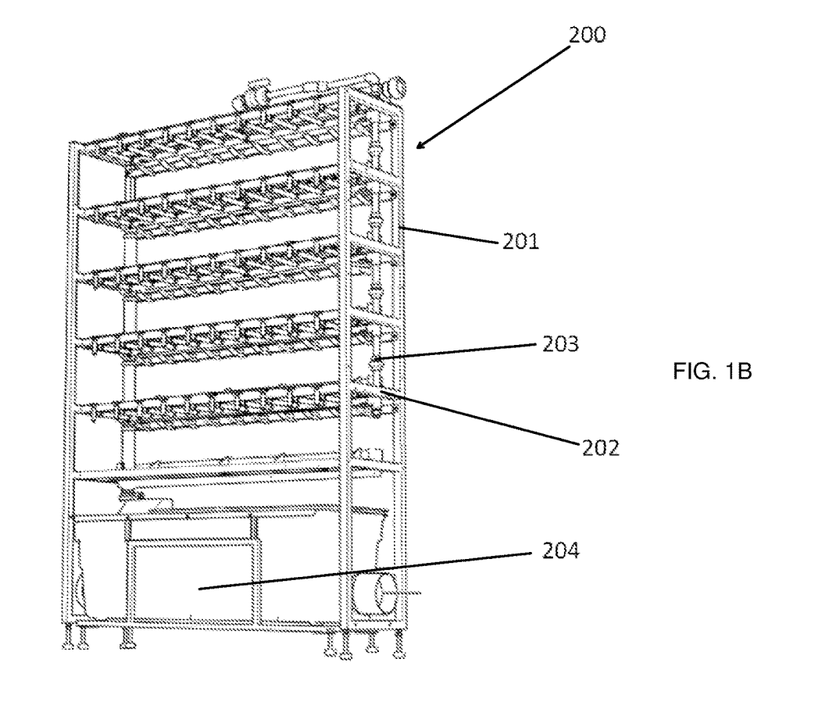

In FIGS. 1A and 1B, the reference numeral 200 identifies an apparatus for breeding laboratory aquatic animal species (small fish or the like); as depicted, the apparatus 200 comprises a shelving (a shelf) 201 including a plurality of shelves 202 arranged mutually in an overlying position, each of said shelves 202 being adapted to support a plurality of trays (not shown for reasons of clarity) arranged side by side and each adapted to contain a predefined amount of maintenance water and therefore to house a predefined number of aquatic animals (variable according to the volume of the tray and the size of the aquatic animals). The trays are mutually connected by a hydraulic circuit including pipes 203 and adapted to allow the circulation of water between the trays, the circuit comprising for this purpose devices housed in a compartment 204 of the shelving 201 and including, for example, pumps, filters and devices typical of every hydraulic circuit.

Since both of said devices for circulating water in the circuit (in the pipes and trays) and the methods of circulating the water itself are substantially known, a detailed description is omitted for synthesis purposes.

Figure 2A:
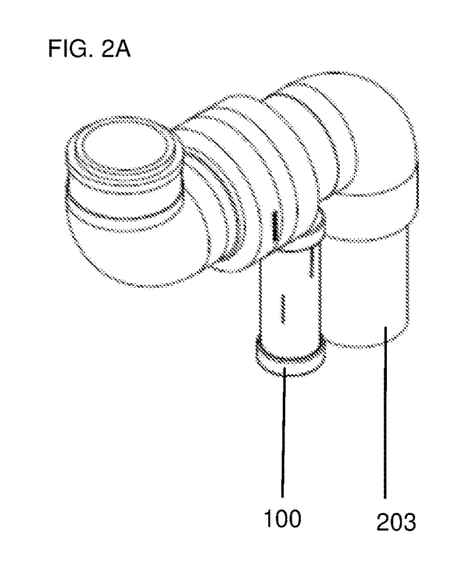
FIGS. 2A and 2B show a perspective and sectional view respectively of an application example of the device according to an embodiment of the present invention to an apparatus of the type depicted in FIGS. 1A and 1B.
Figure 2B:
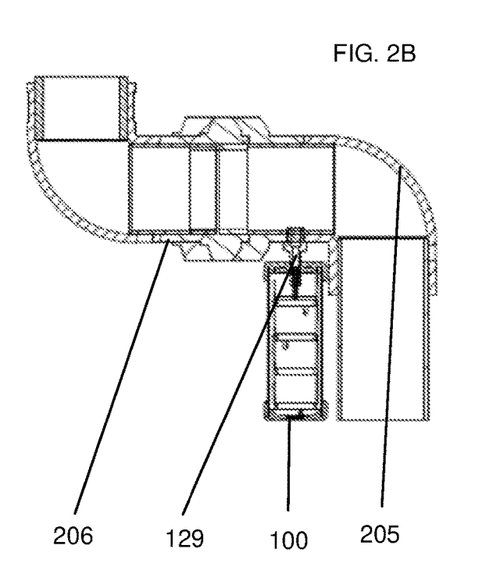

As shown in FIGS. 2a and 2b, a device 100 according to the present invention is installed along the hydraulic circuit of the apparatus 200; in the particular and non-exclusive case of FIGS. 2a and 2b, the device 100 is applied to an elbow 205 of the pipe 203, in particular to a horizontal section 206 of the pipe 203 so that the device 100 is arranged substantially vertically and therefore so that the water in the circuit can be introduced into the device 100 and flow out of the device 100 substantially by gravity; however, different arrangements are possible in which, for example, the device 100 is applied to a vertical section of the pipe 203 so as to be oriented along a substantially horizontal direction. Whatever the orientation thereof (vertical or horizontal or oblique), the device 100 is applied to the section of pipe 203 so as to be in hydraulic communication with the circuit of the apparatus 200, i.e., so as to intercept the flowing of water in circulation in the circuit according to the methods explained in more detail below; in practice, with the device 100 applied to the apparatus 200, part of the water circulating in the apparatus 200 is introduced into the device 100 and discharged from the device 100, where the water discharged from the device 100 can be reintroduced into the circuit of the apparatus 200 or dispersed or accumulated in a container.

In the following, with reference to FIGS. 3 to 10, an embodiment of the device 100 will be described, where in FIGS. 3 to 10 component parts of the device 100 and/or of the apparatus 200 already described with reference to other figures are identified by the same reference numerals.

Figure 9:
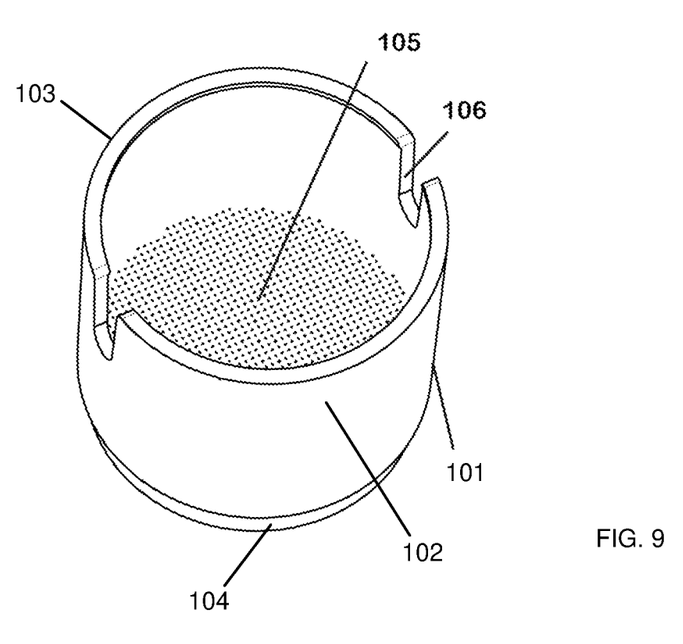
FIGS. 9 and 10 each show a perspective view of a component of a device according to an embodiment of the present invention.
Figure 10:
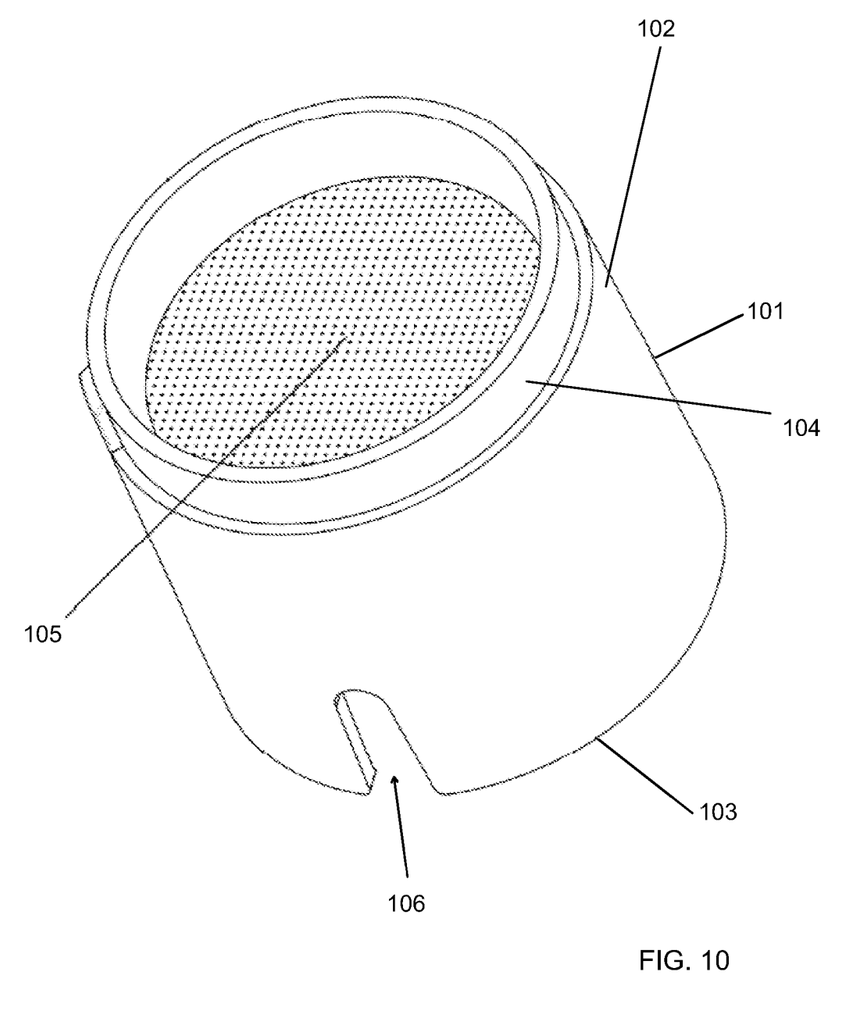

FIGS. 9 and 10 each show a hollow tubular section 101, where the definition hollow "tubular" means a hollow component with any cross-section, and therefore not only circular (as in the case shown) but also, for example, square or polygonal in general, elliptical, etc.

Figure 3:
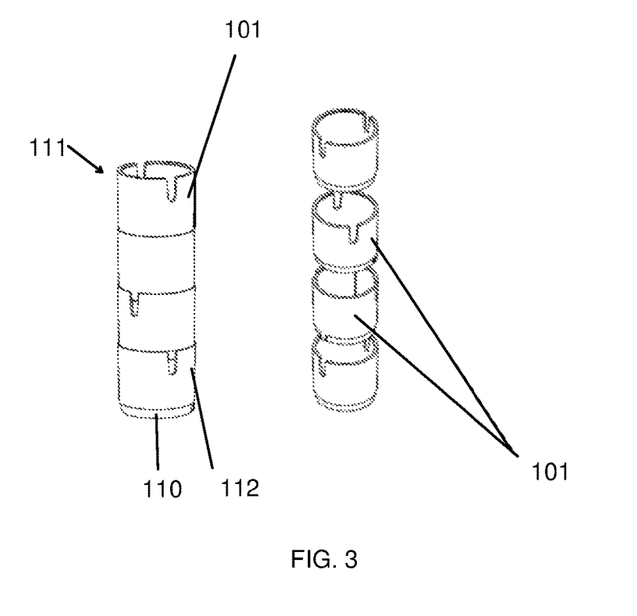
FIG. 3 shows a perspective view of the main body of a device according to an embodiment of the present invention.

Each section 101 therefore comprises an outside wall 102 extending along a direction parallel to the longitudinal axis of symmetry thereof between a first end portion 103 and a second end portion 104 opposite to said first end portion 103, where the second end portion 104 is tapered or in any case shaped so as to be housed in and adjacent first end portion 103 of a second section 101, the sections 101 therefore being adapted to be mutually connected as shown in FIG. 3, i.e., by form and dimension interference between said second end portion 104 of a hollow tubular section 101 with said first end portion 103 of an adjacent hollow tubular section 101.

The mutual connection, in the manner described above, of a plurality of hollow tubular sections 101 (four in number in the non-limiting example of FIG. 3), results in the forming of a hollow tubular body 110 adapted to allow the passage of a liquid (in particular water) therein, between the upstream end 111 and the opposite downstream end 112. Furthermore, as depicted in FIGS. 9 and 10, each section 101 comprises a filtering net or mesh 105 arranged transversely (with respect to the longitudinal axis of symmetry) and including a plurality of micro holes. The filtering net or mesh 105 is made of polyester (PES), where embodiments are possible in which the outside wall 102 is made of a different plastic material, in particular of Polystyrene.

In use, the flowing of breeding water (maintenance or housing) in the main hollow body 110, between the upstream end 111 and the downstream end 112, results in the capture by each net or mesh 105 of organic material and/or inorganic material possibly present in the water, and in particular in the forming, on one or more of the meshes or nets 105, of a film or layer of organic and/or inorganic material, the forming of said film or layer being particularly promoted by both the choice of the size of the micro holes, and by the fact that at least the mesh 105 is made of polyester (PES).

In this regard, according to the present invention, the dimension of the micro holes varies to decrease from the mesh 105 of the end section 101 further upstream to the mesh 105 of the end section 101 further downstream.

In particular, in the case of a main hollow body 110 formed by three sections 101 arranged in succession and mutually connected, the dimension (diameter) of the through-holes of the filtering mesh 105 of the first hollow tubular section 101 further upstream is between 1750 and 2150 μm, the dimension of the through-holes of the filtering mesh 105 of the second (intermediate) hollow tubular section 101 is between 55 and 155 μm, and the dimension of the through-holes of the filtering mesh 105 of the third hollow tubular section further downstream is between 4 and 10 μm.

However, embodiments are also possible in which the main hollow body 110 comprises four sections 101 arranged in succession and mutually connected to form the hollow body 110; in this case, the dimension (diameter) of the through-holes of the filtering mesh 105 of the first hollow tubular section 101 further upstream is between 1750 and 2150 μm, the dimension of the through-holes of the filtering mesh 105 of the second (intermediate) hollow tubular section 101 is between 55 and 155 μm, the dimension of the through-holes of the filtering mesh 105 of the third (intermediate) hollow tubular section is between 4 and 10 μm, whereas the mesh 105 of the fourth section 101 further downstream corresponds to that of the mesh 105 of the third section 101 or, alternatively, the fourth section 101 does not comprise the filtering mesh 105. In regard to the planar dimension of the mesh 105, it is between 400 and 600 sq. mm.

Again as depicted, each section 101 comprises a through notch 106 extending from the free edge of the first end portion 103 parallel to the longitudinal extension direction of the section 101 (of the outside wall 102) and connects the inside of the section 101 with the outside; in particular, the longitudinal extension of the notch 106 is larger than the longitudinal extension of the tapered portion 104 so that, with the sections 101 mutually connected to form the hollow body 110, each notch 106 is not completely obstructed by said tapered portion 104 of the adjacent section 101, but rather defines a through opening. Each notch 106 therefore defines an "overflow" device adapted to discharge any excess water present inside the body 110 to outside the body 110 (for example in the case in which one or more meshes 106 are obstructed by the film or layer of organic and/or inorganic material).

Figure 4:
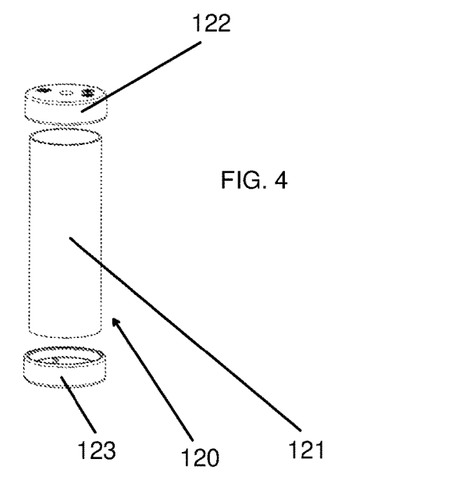
FIG. 4 shows a perspective view of the hollow container of a device according to an embodiment of the present invention.
Figure 7:
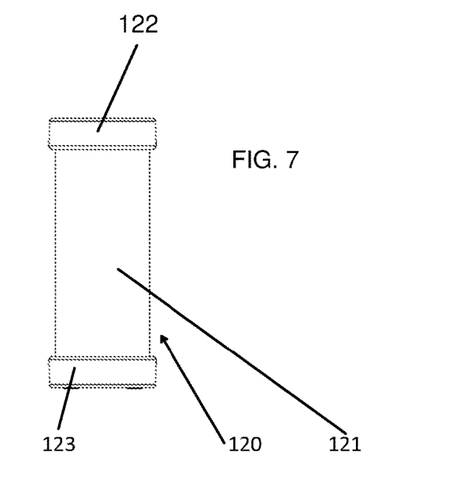
FIG. 7 shows a side view of a device according to an embodiment of the present invention.
Figure 8:
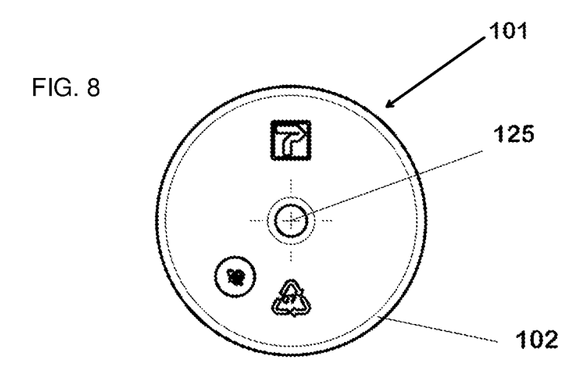
FIG. 8 shows a top plan view of a device according to an embodiment of the present invention.

The figures also show that the device 100 comprises a hollow outer container 120 inside which the hollow body 110 is housed. Referring to FIGS. 4 and 7, the container 120 comprises a hollow element 121 closed at opposite ends by a first plug 122 and a second plug 123, respectively, made of elastic material, for example silicone.

Figures 5A, 5B, 6:
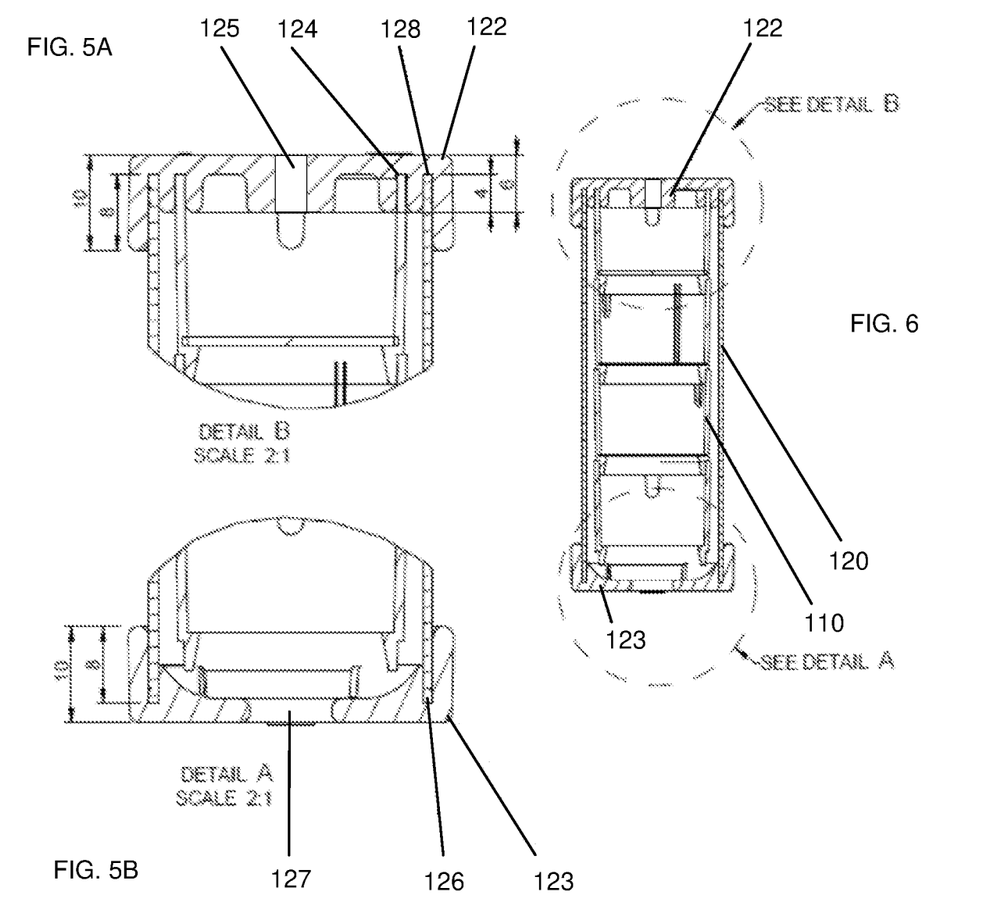
FIGS. 5A and 5B show detailed sectional views of the device according to an embodiment of the present invention.
FIG. 6 shows a longitudinal sectional view of a device according to an embodiment of the present invention.

Referring to FIG. 5A, the first upper plug 122 is shaped to define a first annular seat 128 in which, with the plug 122 in the closed position, the free edge of the upstream end of the container 120 is engaged by form and dimension interference, as well as a second annular seat 124 in which the free edge of the end section 101 further upstream of the body 110 is engaged, said first seat 128 and second seat 124 therefore being concentric with a diameter corresponding to the diameter of the container 120 and respectively of the body 110. The plug 122 further comprises a central through opening 125 (FIG. 8) and means 129 for applying the device 100 to a pipe 203 (as depicted in FIG. 2B), where the through opening 125 allows the introduction of water into the device 100, in particular into the body 110 and/or into the hollow container 120.

The lower plug 123 on the part thereof comprises an annular seat 126 in which, with the plug 123 in the closed position, the free edge of the downstream end of the container 120 is engaged by form and dimension interference, where the plug 123 comprises a through opening 127 for the discharge or outflow of water from the device 100 (FIG. 5B).

The use of the device 100 for microbiological screening of the maintenance water of aquatic animals can be summarized as follows.

With the device 100 applied to the apparatus 200 so as to intercept at least part of the water circulating in the circuit of the apparatus itself 200, the continuous flowing of water through the device 100, entering through the hole 125 and exiting through the hole 127, and therefore through the main hollow body 110, results in the accumulation on the meshes 105 (one or more) of the sections 101, of a layer of organic and/or inorganic material. The forming of one or more layers or films of organic and/or inorganic material can be monitored visually through the container 120 (in transparent material), where upon the forming of one or more layers which can be subjected to laboratory analysis, the device 100 is removed from the apparatus 200 and the sections 101, once the body 110 has been extracted from the container 120, are separated and subjected to analysis of the respective film or layer. Alternatively, the device 100 can be removed from the apparatus 200 according to predefined guidelines, regardless of the degree of accumulation of organic and/or inorganic material on one or more of the meshes or nets 105.

We have thus demonstrated by means of the detailed description of the embodiments of the present invention shown in the drawings given above that the present invention makes it possible to obtain the desired objects and to overcome or at least limit the drawbacks found in the background art.

In particular, by means of the present invention a device for the microbiological screening of the maintenance water of aquatic animal species, in particular laboratory animals, and an apparatus for housing said aquatic animal species are provided, where:
the device 100 ensures reliable monitoring of the housing water of aquatic animal species, in particular laboratory animals;
it is achievable and implementable at low cost and in simple, if not immediate, methods;
it does not involve the use of sentinel animals;
it avoids or at least limits the risk of transmission of pathogens.

The device simultaneously allows to concentrate organic and inorganic material coming from the aquatic colony environment or part thereof over time and promote the development of biofilms in an isolated manner.

The device allows the environmental microbiological monitoring of a defined microbiological unit as a whole.

Through the use of a specific plastic material for the nets or meshes 105, the device promotes the development of the biofilm.

The device offers the ability to filter an amount of recirculated water over time sufficient for the retention of microorganisms or fractions thereof identifiable by PCR.

Although the present invention is explained above by means of a detailed description of the embodiments thereof shown in the drawings, the present invention is obviously not limited to the embodiments described above and shown on the drawings; on the contrary, all the variants and/or changes to the embodiments described and shown on the accompanying drawings will appear obvious and immediate to a person skilled in the art.

The scope of protection of the present invention is thus defined by the claims.

The invention claimed is:

1. A microbiological screening device for collection and concentration of organic and inorganic material present in a liquid, said device comprising:
a plurality of hollow tubular sections arranged one following another, and reciprocally connected, to define a main hollow tubular body configured to allow flowing of a fluid between a first end thereof and a second end thereof, opposite to said first end thereof, wherein every hollow tubular section comprises a filtering mesh or net arranged substantially transversely to a longitudinal extension direction thereof and includes a plurality of through-holes;
wherein a size of said through-holes of each of said filtering meshes is larger than that of the through-holes of the filtering mesh of a next hollow tubular section in the longitudinal extension direction from said first end to said second end; and wherein each of said plurality of hollow tubular sections comprises an overflow device configured to allow the flowing of said liquid from inside of said main hollow tubular body to an outside portion of said main hollow tubular body.

2. The microbiological screening device according to claim 1, wherein each of said filtering meshes is made of polyester (PES) and is adapted to promote a forming of a biofilm usable for microbiological investigations.

3. The device according to claim 1, wherein parts of each of said plurality of hollow tubular sections other than said filtering mesh are made of polystyrene.

4. The microbiological screening device according to claim 1, wherein said plurality of hollow tubular sections are mutually connected by form and dimension interference and adapted to be mutually disconnected.

5. The microbiological screening device according to claim 4, wherein each of said plurality of hollow tubular sections comprises a first end portion and a second end portion, opposite to said first end portion, and wherein said first end portion of each of said plurality of hollow tubular sections is adapted to accommodate, by form and dimension interference, said second end portion of an adjacent hollow tubular section in the longitudinal extension direction from said first end to said second end of said main hollow tubular body.

6. The microbiological screening device according to claim 1, wherein each said overflow device comprises a through-notch made on an outside wall of the respective hollow tubular section, and wherein said through-notch extends from a free edge of a first end portion of each of said plurality of hollow tubular sections.

7. The microbiological screening device according to claim 1, wherein said device comprises a hollow container, wherein said main hollow tubular body formed by said plurality of hollow tubular sections is housed within said hollow container, and wherein an interspace is arranged between an outer surface of said main hollow tubular body and an inner surface of said hollow container.

8. The microbiological screening device according to claim 7, wherein said device comprises a first plug and a second plug removably applied to a first end portion of said hollow container and to a second end portion of said hollow container, respectively, opposite to said first end portion thereof, and wherein said first plug and said second plug include a first through-hole and a second through-hole, respectively, adapted to allow an intake of said liquid into said hollow container and an outflow of said liquid from said hollow container, respectively.

9. The microbiological screening device according to claim 8, wherein said hollow container comprises means adapted to permit an application thereof to a main pipe and to put in communication an inside of said main pipe with the inside of the main hollow tubular body so as to allow flowing of said liquid from said main pipe into said main hollow tubular body.

10. The microbiological screening device according to claim 1, wherein said plurality of hollow tubular sections includes three hollow tubular sections, wherein a first diameter of the through-holes of the filtering mesh of the first hollow tubular section is between 1750 and 2150 µm, wherein a second diameter of the through-holes of the filtering mesh of the second hollow tubular section adjacent to said first hollow tubular section is between 55 and 155 µm, and wherein a third diameter of the through-holes of the filtering mesh of the third hollow tubular section adjacent to said second hollow tubular section is between 4 and 10 µm.

11. The microbiological screening device according to claim 1, wherein said plurality of hollow tubular sections includes four hollow tubular sections, wherein a first diameter of the through-holes of the filtering mesh of the first hollow tubular section is between 1750 and 2150 µm, wherein a second diameter of the through-holes of the filtering mesh of the second hollow tubular section adjacent to said first hollow tubular section is between 55 and 155 µm, and wherein a third diameter of the through-holes of the filtering mesh of the third hollow tubular section adjacent to said second hollow tubular section is between 4 and 10 µm.

12. An apparatus for breeding laboratory aquatic animal species, said apparatus including a plurality of trays each of which being adapted to contain a predefined amount of a liquid and to house a sub-population of these animal species, wherein said plurality of trays are reciprocally connected by means of a circuit adapted to allow circulation of said liquid between said plurality of trays, wherein said apparatus comprises at least the microbiological screening device according to claim 1 applied to said circuit so as to intercept at least part of the liquid in transit within said circuit.

13. The apparatus according to claim 12, wherein said microbiological screening device is applied to said circuit in a position that allows the flowing by gravity of said liquid within said main hollow tubular body.

14. The apparatus according to claim 12, wherein said plurality of trays are arranged on a storage rack comprising superimposed shelves.

* * * * *